(12) United States Patent
Radl et al.

(10) Patent No.: US 7,933,817 B2
(45) Date of Patent: Apr. 26, 2011

(54) BILLING METHOD FOR PUMP USAGE

(75) Inventors: Christopher L. Radl, Malvern, PA (US); Kevin P. Klocek, Wynnewood, PA (US); John Karpowicz, Chester Springs, PA (US); John R. Boehringer, Wynnewood, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 72 days.

(21) Appl. No.: 11/818,337

(22) Filed: Jun. 14, 2007

(65) Prior Publication Data
US 2008/0005000 A1 Jan. 3, 2008

Related U.S. Application Data

(60) Provisional application No. 60/813,582, filed on Jun. 14, 2006.

(51) Int. Cl.
*G07F 19/00* (2006.01)
*H04M 15/00* (2006.01)
*G06Q 10/00* (2006.01)
*G06Q 50/00* (2006.01)
*G06Q 7/00* (2006.01)
*G06F 17/00* (2006.01)

(52) U.S. Cl. .............................. 705/34; 705/2; 705/400
(58) Field of Classification Search .................... 705/34, 705/2; 604/313, 319, 317
See application file for complete search history.

(56) References Cited

U.S. PATENT DOCUMENTS

| | | | | |
|---|---|---|---|---|
| 3,597,794 A | * | 8/1971 | Mann | 425/140 |
| 4,464,172 A | * | 8/1984 | Lichtenstein | 604/65 |
| 5,233,987 A | * | 8/1993 | Fabian et al. | 607/41 |
| 5,258,906 A | * | 11/1993 | Kroll et al. | 705/2 |
| 5,274,545 A | * | 12/1993 | Allan et al. | 368/156 |
| 5,449,347 A | * | 9/1995 | Preen et al. | 604/118 |
| 5,739,508 A | * | 4/1998 | Uber, III | 235/375 |
| 5,819,723 A | * | 10/1998 | Joseph | 128/207.14 |
| 6,049,791 A | * | 4/2000 | Lerner | 705/412 |
| 6,955,664 B2 | * | 10/2005 | D'Antonio | 604/323 |
| 7,181,421 B2 | * | 2/2007 | Peterson et al. | 705/32 |

(Continued)

OTHER PUBLICATIONS

Artificial Heart Opearting point control system: Heart disease weekly, Atlanta, Jul. 27, 2003: p. 12.*

(Continued)

*Primary Examiner* — Matthew S Gart
*Assistant Examiner* — Harshad Parikh
(74) *Attorney, Agent, or Firm* — Caesar, Rivise, Bernstein, Cohen & Pokotilow, Ltd.

(57) ABSTRACT

Disclosed are methods of leasing or billing for the usage of a portable suction pump adapted for use in a suction-assisted would treatment system. The pump has means for recording time units corresponding to periods of time when the pump is operating and for providing reports of usage time. The pump further has means for detecting that the wound treatment system is operating normally so as to be compliant with standards for suction wound treatment, and for recording and reporting time of normal operation or compliant usage. The methods include leasing the pump at a payment schedule that is based upon the amount of actual usage time or the amount of compliant usage time. The lease payment may include an amount of pre-paid time units such that unused time units can be credited to a new or renewed lease for a replacement pump. The billing methods can also be based in whole or in part on a planned maintenance schedule for the pump.

29 Claims, 3 Drawing Sheets

U.S. PATENT DOCUMENTS

| | | | |
|---|---|---|---|
| 7,214,202 B1 * | 5/2007 | Vogel et al. | 601/11 |
| 7,215,109 B2 * | 5/2007 | Angerame et al. | 324/103 R |
| 7,428,497 B2 * | 9/2008 | Agarwal et al. | 705/14.54 |
| 2002/0087341 A1 * | 7/2002 | Kappel et al. | 705/1 |
| 2005/0096941 A1 * | 5/2005 | Tong | 705/2 |
| 2005/0154359 A1 * | 7/2005 | Charlez | 604/317 |
| 2007/0033071 A1 * | 2/2007 | Schmieding | 705/2 |
| 2007/0118397 A1 * | 5/2007 | Williams et al. | 705/2 |
| 2008/0077091 A1 * | 3/2008 | Mulligan | 604/147 |
| 2008/0154187 A1 * | 6/2008 | Krulevitch et al. | 604/48 |
| 2008/0287892 A1 * | 11/2008 | Khan et al. | 604/313 |
| 2010/0081919 A1 * | 4/2010 | Hyde et al. | 600/411 |

OTHER PUBLICATIONS

Peoplesoft First to deliver Vertical solutions, Business wire, Aug. 26, 2002.*

New ideas improve products, Machinery & Equipment by Don Mills Feb. 1998, vol. 14 Issue 1, p. 18.*

A closer look at hydraulic variable pumps: Design Engineering: Toronto, Mar. 1995 vol. 41 Iss 3, p. 16.*

TEOCO' new Xtrac utilizes Datawatch's Monarch Data pump software: Business wire: Dec. 6, 2005.*

* cited by examiner

BILLING METHOD FOR PUMP USAGE

REFERENCE TO RELATED APPLICATIONS

This application claims priority of U.S. Provisional Application No. 60/813,582 filed Jun. 14, 2006.

FIELD OF THE INVENTION

This invention relates to the general field of methods of billing for use of medical equipment; and to the more particular field of billing for the use of portable suction pumps to provide suction for wound therapy.

BACKGROUND OF THE INVENTION

In wound therapy systems that use suction for drainage or other healing modalities, the suction may be either supplied by a main suction pump via a stationary in-wall air manifold and pressure regulator, or by a portable suction pump that can be moved on a bed or stand along with the patient. Charges for the use of the in-wall system are generally included in the treatment billing schedules and are thus not separate billable items to a patient, but portable pumps are often leased to a health care provider or patient, and the rental charges may appear as separate billable items in patient medical bills.

However, the rental charges to a health care provider are usually billed either as a single flat charge per patient or based on the duration of rental measured in days, and are not calculated for time of actual usage or for time of compliant usage in suction wound therapy. Usage is defined as usage of a pump for wound therapy whether or not suction is being adequately applied to the wound. Compliant usage is defined as usage where medically effective suction is applied to the wound. Time of compliant usage is defined as time during which medically effective suction is applied to the wound. In some instances, a contract for leased pump usage may provide that billing is based upon notification of use/non-use to the leasing agency by personnel at the medical facility or health care provider. In that example, usage is presumed to begin when the pump is delivered and to continue every day thereafter unless the medical facility notifies the leasing agency that the pump has not been used for that day or for a period of days. If the medical facility neglects to notify the leasing agency of periods of non-use, the medical facility is billed for each day whether or not the pump was in use.

Thus, where medical health care reimbursement is tied to specific treatment codes, the reimbursement schedule may be established according to purported medians of usage without the ability to adjust for usage time or compliant usage time. In any endeavor to reduce or refine the charges and reimbursements for suction wound therapy, it would be advantageous to have the ability to charge only for usage time or for compliant usage time of a portable suction pump.

The ability to bill based on usage or compliant usage may be particularly important in view of the growing trend towards pay-for-performance billing. Until recently, the health care industry has operated primarily on a pay-for-service structure, in which health care providers are paid according to the health services provided to patients, rather than on the quality or effectiveness of that care. The goal of pay-for-performance is to improve the quality and effectiveness of health care, and as a corollary benefit, to reduce costs. In order for pay-for-performance to achieve these goals, the measures should be scientifically sound and the data must be feasible to collect and analyze. In particular with regard to suction wound therapy, the pump is only capable of providing therapy when it is operating, and therefore billing based on usage time would be one performance-based measure. Moreover, the therapy is only effective for the time when the wound is subjected to a therapeutic level of suction, and therefore billing based on compliant usage time would be a reasonable measure of the quality of therapy.

Portable pumps may also require periodic cleaning, maintenance inspections, preventive replacement of critical parts before mean time to failure, and/or calibration of sensors. Hence, another potentially attractive leasing method is to rent the pump for a period of time corresponding to a planned maintenance interval. In that manner, the pump may periodically be exchanged for a freshly inspected and calibrated replacement pump. The same periodic exchange could be incorporated as part of a sale/repurchase arrangement that would operate similar to rental arrangement. In this application, the term "lease" and its derivatives should be understood to include both rental and sale/repurchase arrangements. Timing the lease to correspond with a planned maintenance interval reduces any incentive to keep the pump operating beyond a period in which it should be inspected and/or repaired, and the ability to exchange for a fresh replacement pump provides convenience for inspection and maintenance without disrupting medical treatment. If a lease term is related to a planned maintenance schedule, it would be advantageous to have the ability to charge only for pump usage time or only for compliant usage time.

In an attempt to make billing for pump usage more rational and efficient, and to provide the safety incentives of a pump lease and exchange program, the present invention provides billing methods directed to the above objectives.

These billing methods can be particularly effective in conjunction with a portable pump having means to monitor normal operation and abnormal operation that would indicate occlusion or air leakage in the negative pressure portion of a suction wound treatment system, the pump further having means to time, record, accumulate, and report or display, in time units, the pump usage time and system normal operation time. Examples of such pumps are described in pending U.S. patent application Ser. No. 11/268,212, filed Nov. 7, 2005 and assigned to Boehringer Laboratories, Inc., and in pending U.S. patent application Ser. No. 11/786,475, filed Apr. 13, 2007 and assigned to Boehringer Technologies LP. The contents of those applications are incorporated herein by reference, and some of the content is repeated herein for the reader's convenience.

SUMMARY OF THE INVENTION

In one aspect, the invention provides a method of billing for the usage of a portable suction pump adapted for use in a suction-assisted wound treatment system, by providing a portable suction pump adapted for recording time units of compliant usage and billing for the pump at a payment schedule that is based at least in part upon the recorded compliant usage time units. Compliant usage of the pump is deemed to be usage of the pump during which medically effective suction or negative pressure is being applied to the wound. The pump can be further adapted for reporting recorded time units and for assessing a fee for such reports.

In another aspect, the invention provides a method of leasing a portable suction pump for suction-assisted wound treatment, by providing a portable suction pump capable of delivering a predetermined amount of compliant usage and computing a lease payment component corresponding to the predetermined amount of compliant usage. The pump can be further adapted for recording an amount of compliant usage, comparing the amount of compliant usage with the predetermined amount of compliant usage, and determining an amount of unused compliant usage for which a credit or partial return of payment may be granted.

In another aspect, the invention provides a method of leasing a portable suction pump for suction-assisted wound treatment, by providing a portable suction pump capable of delivering an amount of pre-programmed time units corresponding to a pump maintenance schedule, computing a lease payment component corresponding to the amount of pre-programmed time units, and establishing a lease term based on the amount of pre-programmed time units and the pump maintenance schedule.

In another aspect, the invention provides a method of leasing a portable suction pump in a suction-assisted wound treatment system, wherein the pump has means for detecting normal operation of the system as defined by operation during which compliant treatment (compliant usage) is being provided. The pump is adapted to record time units of usage and of compliant usage, and is further adapted to determine a compliant treatment factor by relating the usage time units and the compliant usage units to a compliant treatment standard. The pump is leased at a payment schedule based at least in part on a compliant treatment factor.

In another aspect, the invention provides a method of billing for usage of suction-assisted wound treatment by detecting normal operation of the system using a flow rate monitor, recording time units of normal operation, and billing at a payment schedule based at least in part upon the recorded normal operation time units.

In another aspect, the invention provides a method of billing for the usage of a portable suction pump adapted for use in a suction-assisted wound treatment system, by providing a portable suction pump adapted for recording time units of usage and billing for the pump at a payment schedule that is based at least in part upon the recorded usage time units. The pump can be further adapted for reporting recorded time units and for assessing a fee for such reports.

In another aspect, the invention provides a portable suction pump adapted for use in a suction-assisted wound treatment system. The pump includes a flow rate monitor for detecting compliant operation of the system and a timing subsystem for recording time units of compliant operation. The pump can be leased on a payment schedule that is based at least in part on the recorded compliant operation time units. Compliant operation is defined as operation where a medically effective suction is applied to the wound.

DESCRIPTION OF PREFERRED
EMBODIMENTS OF THE INVENTION

Figure 1:
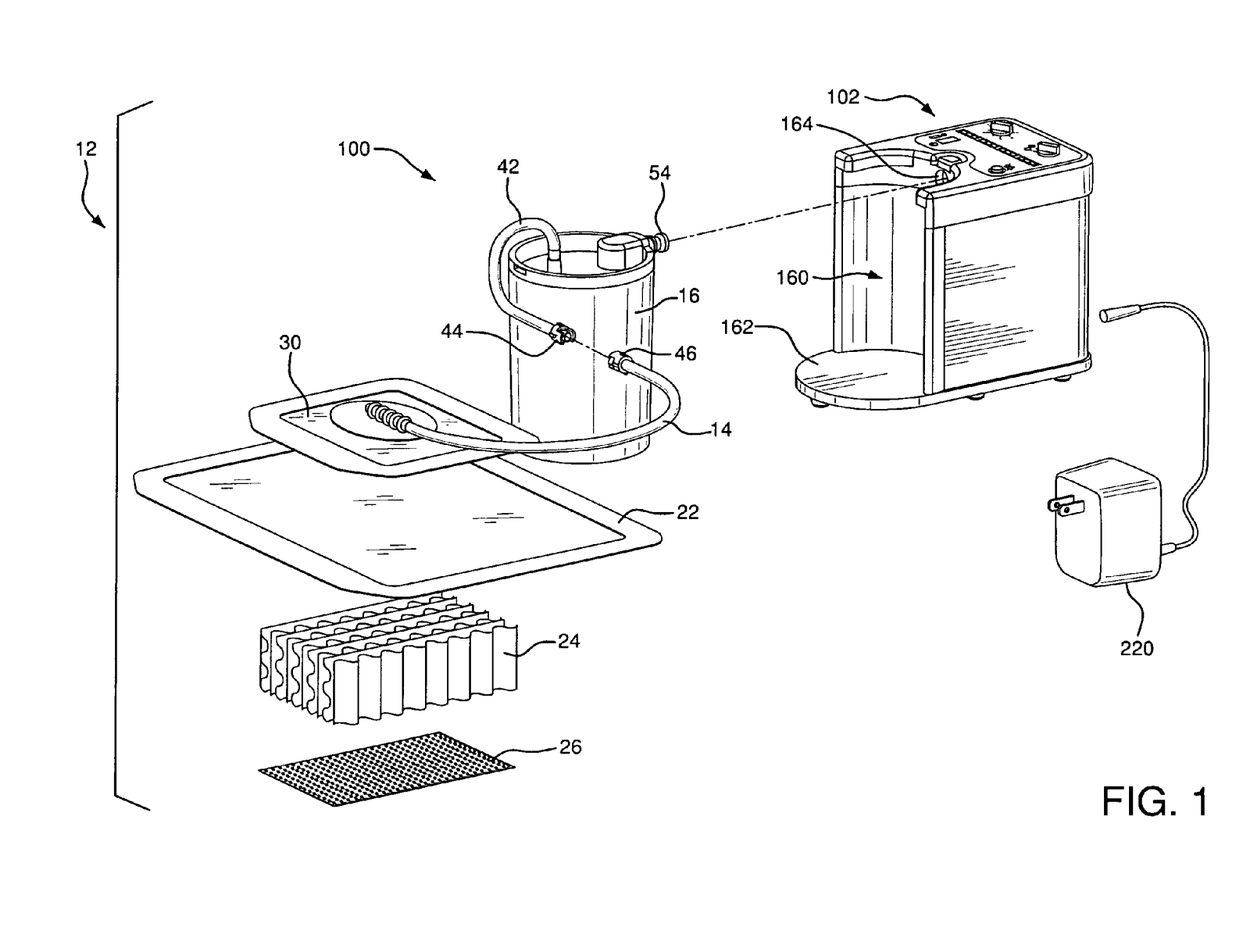
FIG. 1 is an exploded perspective view of an embodiment of a suction-assisted wound treatment system having a portable pump.

FIG. 1 depicts an embodiment of a suction-assisted wound treatment system (100) using a portable suction pump unit (102). The wound treatment system (100) comprises a wound dressing (12) including a wound cover (22) and wound packing material (24), and may further include a wound contact layer (26). A suction tube (14) terminates at a tube attachment patch (30) which allows the tube (14) to communicate through a slit in the cover (22). A calibrated vent (not shown) may be provided in the suction tube (14) to provide a reference airflow rate. The system (100) also includes a waste collection canister (16) for collecting fluids aspirated from the wound.

Exemplary elements or components for use in a suction-assisted wound treatment system are described in greater detail in pending U.S. patent application Ser. Nos. 11/268,212 and 11/786,475. There are, however, a wide variety of each of these components of a suction wound dressing system. The present invention is not intended to be limited to these components.

Figure 2:
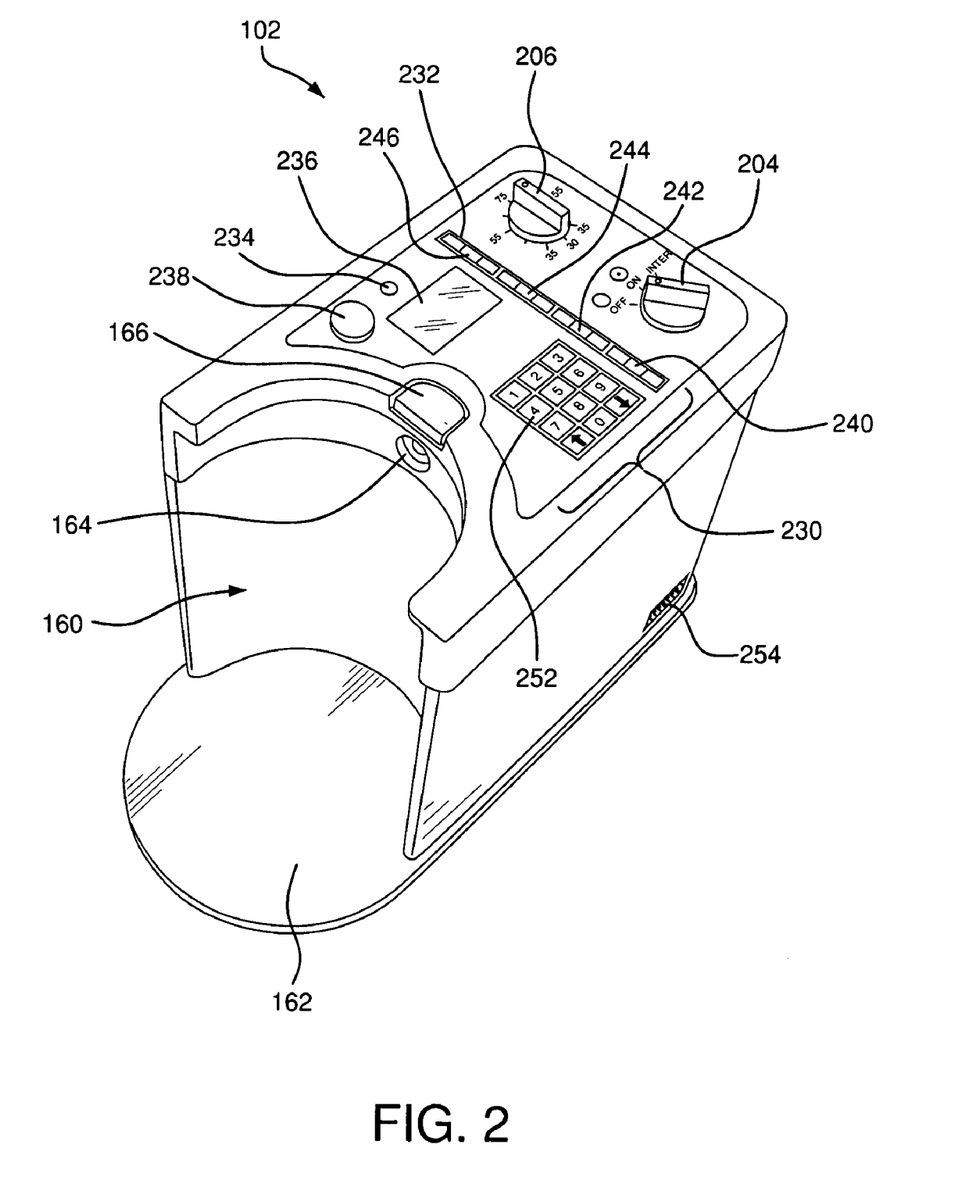
FIG. 2 is a perspective view of the pump showing visual indicators for displaying compliant and/or non-compliant system operation and for reporting cumulative time units.
Figure 3:
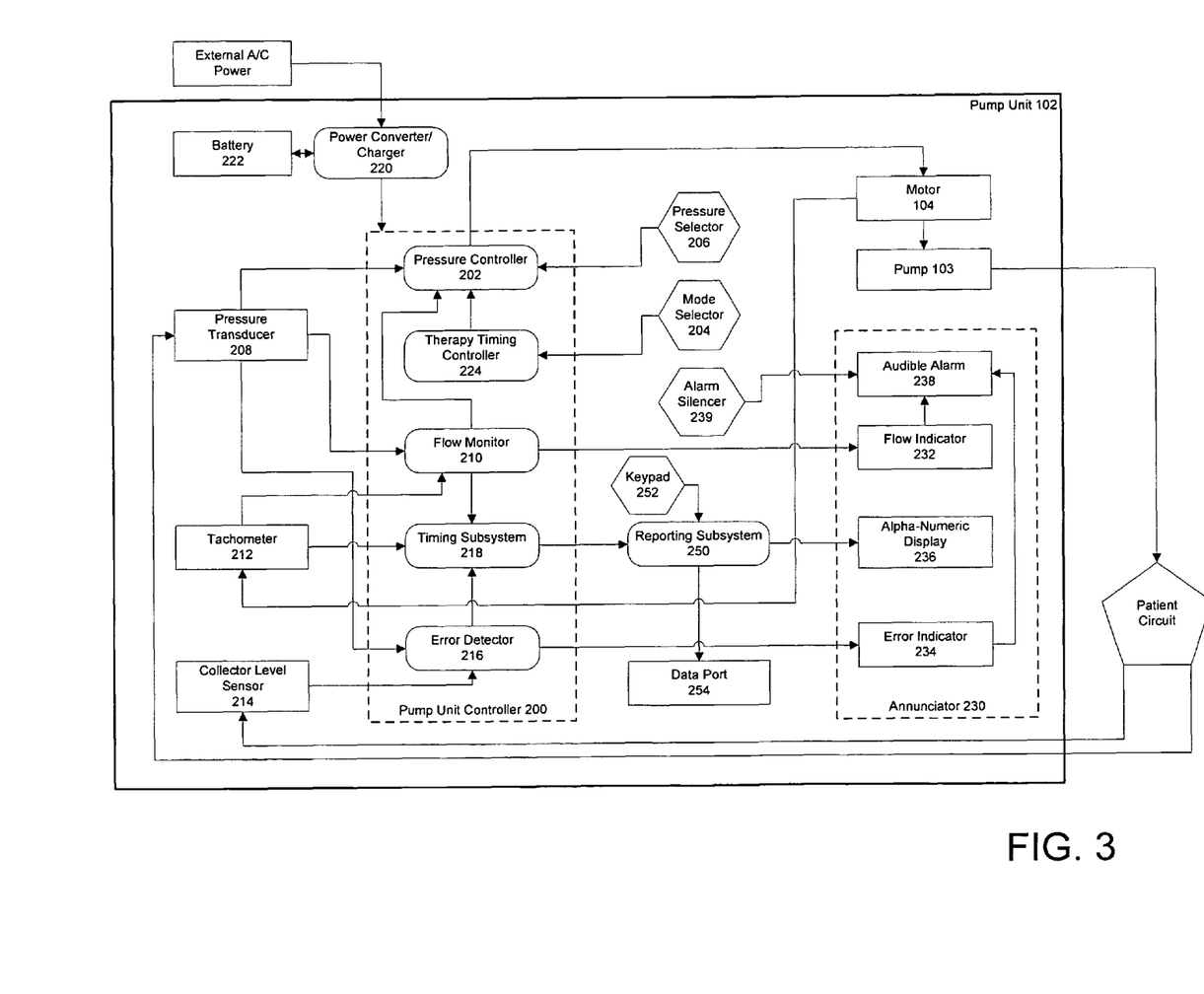
FIG. 3 is a schematic diagram of a pump including a timing subsystem and a reporting subsystem that are used to measure, record, accumulate, and report or display time units of pump operation and of compliant system operation.

FIG. 2 depicts an exemplary portable suction pump unit (102), and FIG. 3 depicts a schematic of a control system for the pump unit (102). The pump unit (102) has an onboard battery power source for operating on low voltage DC power, and can also be run on AC wall power with a suitable power converter, which may be combined with a battery charger to charge the battery during use. The pump unit (102) is turned On using a mode selector switch (204) capable of selecting between On, Off, and Intermittent modes, although a simple On/Off power switch could be used instead. Intermittent control may be used to provide intermittent high/low therapeutic suction to a wound in accordance with some treatment protocols. It is known to treat wounds with intermittent suction where suction is applied for a controlled period of time and then suction is stopped for a controlled period of time. For example the controlled period of time when suction is applied can be 5 minutes and the controlled period of time when suction is stopped can be 2 minutes, for a total intermitting cycle time of 7 minutes. In such a situation, compliant usage time would include the controlled period when suction is turned off if the appropriate amount of suction is applied in the period before and after the period when suction is off. The portable pump unit (102) is configured to provide controlled levels of suction to the wound, for example as selected by the pressure selector dial (206).

The pump unit (102) has a flow rate monitor (232) or other means to detect and indicate normal and/or abnormal conditions of operation. Various devices for flow rate monitoring are disclosed in pending U.S. patent application Ser. Nos. 11/268,212 and 11/786,475. In addition, when the portable pump unit (102) includes a positive displacement pump (103), it is possible to monitor pump motor speed with a tachometer (212) as a surrogate for airflow rate. For purposes of this invention, any parameter indicative of flow rate into the pump can be used to monitor flow rate to indicate normal/abnormal operation.

A flow rate that is comparable to or within a range of the reference flow rate indicates normal operation. A flow rate that is less than the reference flow indicates an abnormal operation of the wound treatment system, likely caused by a blockage or crimp in the lines or a full collection canister. A flow rate that is higher than the reference flow rate indicates abnormal operation, likely caused by leakage in the wound dressing. Alarms alert the caregiver to inspect the seal of the wound cover or other potential leaks in the system. Normal operation can be defined by a flow rate in a range within a specified percentage deviation about the reference flow rate.

As shown in FIG. 3, a pump unit controller (200) of the pump unit (102) has a timing subsystem (218) for recording time units corresponding to periods of time when a motor (104) driving the pump (103) is running, and for accumulating corresponding time unit data. Preferably the timing subsystem (218) records and accumulates the pump operating time units based upon inputs from various sensors. For example, the timing can be started and stopped by signals from the mode selector switch (204), or signals that can detect when the pump is running from the tachometer (212) or other sensor. The pump unit (102) further has a reporting subsystem (250) capable of providing time reports of the time history of operation of the pump (103). The time reports can include a record of usage time intervals, a record of the date and duration of usage time intervals, a record of total accumulated usage time, a record of accumulated compliant usage time, and a record of usage time remaining on a preset usage time period.

The timing subsystem (218) and the reporting subsystem (250) of the pump unit controller (200) may include an onboard compliance monitor as part of the timing function. A user-viewable alpha-numeric display (236) alerts the caregiver to deviations from normal application of suction to the wound over time and is a useful adjunct to the application of suction wound therapy. The compliance monitor may compute the number of hours that suction has been within a range of a pressure setpoint. For example, compliance can be designated as suction with a range of about ±25 mm Hg about a pressure setpoint. Preferably, compliance is designated as suction within a range of about ±10 mm Hg about a pressure setpoint. More preferably, compliance is designated as suction within a range of about ±5 mm Hg. Medical experience has shown that suction is preferably applied for at least 22 of any 24 continuous hours to be effective. The display (236) can show and record in numerous ways the number or percentage of compliant hours of suction therapy for a given therapy period.

It is common practice for clinicians to order negative pressure wound therapy according to a standing order or prescription and it is anticipated that such orders follow standard practice. Parameters that may be specified in standing orders or prescriptions include, but are not limited to, suction level, duration of suction application, amount of suction applied per day, use of intermitting suction, frequency of dressing changes, type of dressing to be employed, and adjunctive therapies. A compliant treatment standard can be a prescribed amount of compliant treatment that is specified by a medical professional, a medical authority, or a manufacturer. The pump may be adapted to record time units of usage and of compliant usage, and further adapted to determine a compliant treatment factor by relating the usage units and the compliant usage units to a compliant treatment standard. A compliant treatment standard can be based on one or more of various parameters, including but not limited to suction level and duration of suction application.

The timing subsystem (218) and reporting subsystem (250) may be connected to alarms which indicate abnormal operating conditions due to leak or occlusion. The reporting subsystem (250) may also be used to indicate time remaining until scheduled maintenance or cleaning, or to indicate time used or remaining on a billing plan where the payments for usage are based upon time units either on return or pre-paid in advance. When the pump unit (102) is sold or leased in this manner, the timing subsystem (218) has the ability to record and accumulate time units corresponding to periods of time when the pump (103) is running (i.e., usage time) and the reporting subsystem (250) has the ability to provide reports of usage time, including compliant usage time when the wound treatment system (100) is operating normally.

The pump unit (102) may have one or more user interfaces for enabling interaction with the timing subsystem (218) and the reporting subsystem (250). In an example, the pump unit (102) can have a keypad (252) for enabling a user to input data. The keypad (252) can be used to enter an authorization key for increasing the preset time units in the timing subsystem (218), a patient identity number or a billing number into the reporting subsystem (250), and/or other information. The keypad (252) can also be used to request that the reporting subsystem (250) generate and output one or more particular reports. In another example, the pump unit (102) can include a USB or memory card port to allow a single-use SIM card to be installed for loading or reloading hours into the timing subsystem (218). In yet another example, the pump unit (102) can have a data port (254) for enabling direct electronic communication between the reporting subsystem (250) and an external electronic device. The data port (254) may be adapted for connection to a computer, a modem, or a computer network, using means including but not limited to a serial or parallel communications port, a wired RJ45 connection, a directional RF connection, wireless or Bluetooth connections under an 802.11 protocol, or other electronic communications mechanism. These or similar connections would enable the pump unit (102) to communicate with other hospital equipment, such as through central station monitoring, or with remote on-site or off-site equipment using the internet. These or similar connections would also enable a pump unit to be monitored and diagnosed remotely. In still another example, the data port (254) can be adapted for direct plug-in of a portable device such as a PDA for enabling a user to request reports, download data and reports, and/or reprogram the pump unit.

With regard to a pump unit (102) having a data port (254) that is equipped to enable downloading of reports to a PDA, computer, or other similar device for processing and viewing data, the billing method can include assessing a fee component based on the type of report that is generated and/or the frequency of such reports. One or more standard reports could be included in the programming of the reporting subsystem (252) or customized reports could be generated based on user input, and the fee can be varied accordingly. These types of data reports can be particularly valuable to a medical facility for optimizing the use of suction wound therapy or for assisting in troubleshooting the causes of non-compliant usage time so that training of staff and/or patients can be focused to remedy those causes.

Various data recorded and accumulated by the timing subsystem (218) and reported by the reporting subsystem (250), including data of operating time units and compliant operating time units, can be used to provide improved billing through the following methods.

A. Pre-paid Hours Method

In a pre-paid hours method, the pump is leased by a lease payment, purchased by a purchase payment, or purchased on a purchase payment schedule, wherein the lease payment, purchase payment, or purchase payment schedule includes a payment component corresponding to a selected amount of operating (usage) time or compliant operating (usage) time. The payment may be a pre-payment made by the medical facility prior to delivery of the pump to the medical facility. When a medical facility returns the pump to a service center for maintenance and/or calibration or exchange for a fresh replacement pump, the unused time may be credited to the medical facility's account and applied to the operating time payment component of the lease payment, purchase payment, or purchase payment schedule for the replacement pump. The credit may be on an hourly proration or a determined-interval proration schedule.

In an embodiment, the initial pre-programmed amount of operating time has been determined to be consistent with anticipated usage during a planned maintenance/calibration interval. As an example of this method, consider a situation where a recommended maintenance/calibration schedule for a portable suction pump has been determined to be six months of usage, and the estimated operating hours of such usage is 1500 hours (i.e., 250 hours per month). The payment or payment schedule for the pump will include a payment component for the full 1500 hours. At a convenient time near the six month date from purchase or lease, the pump is returned to a service center for cleaning, recalibration, and any preventive or restorative maintenance as indicated by the pump's condition and operating history. At this time, the returned pump may also be updated to current specifications.

To avoid disrupting the ability of the medical facility to provide suction wound treatment, the returned pump is exchanged for a replacement pump. Upon exchange, based on data recorded by a cumulative timer on the returned pump, it is determined that the pump was used for 1460 hours. (It should be noted that alternatively, the time of usage could be manually recorded. The manually recorded time of usage can be reported when the pump is returned, or it can be periodically communicated by telephone, fax, e-mail, internet communications, or other means.) Accordingly, pursuant to the billing method, the required payment for the replacement pump will be decreased by crediting the medical facility's account for the 40 unused hours and applying that credit to the replacement pump. Thus, the replacement pump will have its timer set for 1500 hours, but the payment component for these hours will be adjusted to include a credit for unused hours on the returned pump. The credit can be an linear hourly proration (i.e., $40/1500$) or a determined interval that may be linear or non-linear (e.g., $100 credit for the first 10 unused hours, $110 credit for the next 10 unused hours, $125 credit for the next 10 unused hours, etc.). Alternatively, the replacement pump could have its timer set for 1540 hours while the account is charged the lease price including a payment component for 1500 hours.

If the medical facility uses the pump for more than 1500 hours during the six month period, the purchase or lease agreement can either permit the additional use for free or stipulate an additional charge for the excess hours, again either prorated or based on a determined interval method. Any excess charges could be payable when the pump is returned. (Alternatively, excess hours could be subtracted from the timer set on the replacement pump.) However, if patient safety concerns set a prudent upper safety limit, such as 1800 hours, on use of a pump without recalibration or inspection, the pump control may contain a disabling switch in communication with the timer to disable pump operation at the prudent safety limit.

If heavy usage would indicate the need for calibration or maintenance earlier than six months and the pump has a safety limit disabling device programmed to 1800 hours, as described above, the device may include means for the user to reset the upper limit with an authorization key. For example, the medical facility may telephone the pump service facility and describe the results of an inspection of certain wear-prone or critical components of the pump, such as couplings and seals, and may provide other indications that the pump is performing well despite heavier than normal usage. The service facility could then send the medical facility a key code or similar authorization to unlock the disablement and reset the pump to run for an additional period. The disablement could also be unlocked by direct local or remote electronic device connected to the data port on the pump.

Similarly, the billing method could include an ability to add time units at a standard rate (e.g., pro rata or based on determined intervals) if the 1500 hours were passed before the expiration of the six month period and the pump appears to be in good working order. If the 1500 hours were approaching in the 3-5 month period, an act could enable the pump unit to operate for an additional amount deemed safe, at the normal fee schedule. The act could include notifying the service facility by phone or e-mail that the pump has been operating for a high amount of time but appears to be functioning properly, entering a key code or similar authorization, and/or electronically uploading or adding time units to the pump.

B. Compliant Use Billing Method.

In addition to billing for time intervals when the pump is turned "On" and running, a pump monitoring system as disclosed in pending U.S. patent application Ser. Nos. 11/268,212 and 11/786,475, and/or as depicted in FIGS. 2 and 3, allows the measurement of compliant time intervals, or time intervals when the pump is sensing normal operation of a suction or negative pressure wound treatment system applied to a patient. This would eliminate charges for pump operation merely for system testing or staff training that should not normally be billed to a patient or reimbursement payer for patient treatment services.

For example, compliance can be defined as medically effective suction being applied to a wound as indicated by normal operation on the pump monitoring system. In normal operation, for example, there is minimal leakage and suction is within a specified percentage deviation from the desired suction (as indicated, for example, by flow through the suction pump being within a range of a reference flow rate), for a continuous period of selected duration. Thus, while the pump can monitor total operating time units for purposes of maintenance and safety, the billing charge may be based upon the actual time of effective use of a suction-assisted treatment, or compliant operating time, as determined by the pump monitoring system. In an alternate embodiment, billing can be based in part upon a ratio of compliant operating time to total operating time, such that the billing rate could be adjusted downward in response to a high ratio of compliance.

In a further alternate embodiment, billing can be based upon the total time of pump usage and the pump can be adapted to automatically stop operating if non-compliant or abnormal operation is detected for a period of time. In an example, if the non-compliant operation is detected at any time during pump operation, a non-compliant timer is started. When the non-compliant timer reaches a predetermined limit, the pump is turned off. The predetermined non-compliant time limit can be a fixed amount of time or can be based on factors including but not limited to the ratio of compliant to non-compliant time since the pump started operating.

In either total-time billing or compliant-time billing, the timing subsystem can be adapted to extract time interval data from the pump and to supply that data to the reporting subsystem to generate a report. A report can indicate pump performance, including pump usage time, compliant usage time, and fault or occlusion time, all as a percent of total time. Additionally, the report can be keyed to a specific time period. The report can be customized around any of these parameters; such customized reports may be particularly useful where medical cost reimbursement from government or private insurers is based in whole or in part on efficacy criteria.

The timing subsystem can further be adapted to assign compliant or non-compliant usage time to a time/date array. This array facilitates the assignment of cause to a non-compliant time period. For example, if it is determined that non-compliance appears to occur regularly in a repeatable time period, such as in the evening, then training can be directed to the medical facility staff who are most responsible for treatment activity during that time period or to a patient using the pump as an out-patient.

While the invention has been disclosed with reference to certain preferred embodiments, numerous modifications, alterations, and changes to the described embodiments are possible without departing from the sphere and scope of the invention, as defined in the appended claims and equivalents thereof. Accordingly, it is intended that the invention not be limited to the described embodiments, but that it have the full scope defined by the language of the following claims.

We claim:

1. A method of billing for the usage of a portable suction pump for suction-assisted wound treatment, the method comprising the steps of:
   (a) providing a portable suction pump to a user for treating a wound;
   (b) inputting data, by the user, into a user interface of the pump, the data related to compliant operation of the pump, wherein compliant operation is operation of the pump when medically effective suction is being applied to a wound;
   (c) operating the pump by the user;
   (d) measuring pump negative pressure from the wound using an instrumentation sensor selected from the group consisting of a pressure sensor and a flow sensor;
   (e) determining the compliant operation of the pump by a monitoring system of the pump;
   (f) recording and accumulating time units of compliant operation by a timing subsystem of the pump,
   (g) reporting time units of compliant operation by a reporting subsystem of the pump; and
   (h) billing for the pump at a payment schedule that is based at least in part upon the recorded compliant operation.

2. The method as in claim 1, further comprising the steps of:
   including in the payment schedule a pre-payment for pre-programmed time units;
   comparing the recorded time units of compliant operation with the pre-programmed time units to determine unused time units; and
   providing a credit or partial return of payment for said unused time units.

3. The method as in claim 2, the method further comprising the step of:
   changing the pre-programmed time units using the user interface.

4. The method as in claim 1, the pump further being adapted for reporting recorded time units, the method further comprising the steps of:
   requesting a report from the pump using the user interface; and
   receiving the report from the pump using the user interface.

5. The method as in claim 4, further comprising the step of:
   assessing a fee corresponding to the report.

6. The method as in claim 4, wherein the user interface comprises one or more of a keypad, a user-viewable display, and a data port for connecting to an electronic device adapted for requesting and/or receiving the report.

7. The method of billing of claim 1, wherein compliant operation is when suction is in a predetermined range about a pressure setpoint, wherein the pressure setpoint is a pressure value selectable by an operator.

8. The method of billing of claim 7, wherein the predetermined range about a pressure setpoint is a range of about ±25 mm Hg about the pressure setpoint.

9. A method of leasing a portable suction pump for suction-assisted wound treatment, the method comprising the steps of:
   (a) providing a portable suction pump to a user for treating a wound,
   (b) inputting data, by the user into a user interface of the pump, the data related to compliant operation of the pump, wherein compliant operation is operation of the pump when medically effective suction is being applied to a wound;
   (c) operating the pump by the user;
   (d) measuring pump negative pressure from the wound using an instrumentation sensor selected from the group consisting of a pressure sensor and a flow sensor;
   (e) determining the compliant operation of the pump by a monitoring system of the pump;
   (f) recording and accumulating time units of compliant operation by a timing subsystem of the pump capable of delivering a predetermined quantity of time units of compliant operation,
   (g) reporting time units of compliant operation by a reporting subsystem of the pump; and
   (h) computing a lease payment component corresponding to the predetermined amount of compliant operation.

10. The method as in claim 9, further comprising the steps of:
    comparing the recorded amount of time units of compliant operation with the predetermined quantity of time units of compliant operation to determine an amount of unused compliant operation; and
    providing a credit or partial return of payment corresponding to the amount of unused compliant operation.

11. The method as in claim 8, further comprising the steps of:
    providing a lease option to return the pump for a replacement pump; and
    applying the credit or partial return of payment to a lease payment for the replacement pump.

12. The method as in claim 9, further comprising the steps of:
    requesting a report from the pump using the user interface; and
    receiving the report from the pump using the user interface.

13. The method as in claim 12, further including the step of: assessing a fee corresponding to the report.

14. The method as in claim 9, wherein the user interface comprises one or more of a keypad, a user-viewable display, and a data port for connecting to an electronic device adapted for requesting and/or receiving the report.

15. The method of billing of claim 9, wherein compliant operation is when suction is in a predetermined range about a pressure setpoint, wherein the pressure setpoint is a pressure value selectable by an operator.

16. The method of billing of claim 15, wherein the predetermined range about a pressure setpoint is a range of about ±25 mm Hg about the pressure setpoint.

17. A method of leasing a portable suction pump in a suction-assisted wound treatment system, comprising:
    (a) providing the pump to a user for treating a wound, the pump having means for detecting compliant operation of the system, the pump being adapted for recording operation time units and for recording compliant operation time units, wherein compliant operation time units are time units where operation of the pump causes medically effective suction to be applied to a wound, (b) inputting data, by the user into a user interface of the pump, the data related to compliant operation of the pump;

(c) operating the pump by the user;

(d) measuring pump negative pressure from the wound using an instrumentation sensor selected from the group consisting of a pressure sensor and a flow sensor;

(e) determining the compliant operation of the pump by a monitoring system of the pump;

(f) recording and accumulating time units of operation by a timing subsystem of the pump;

(g) recording and accumulating time units of compliant operation by the timing subsystem of the pump, (h) relating the accumulated time units of operation and the accumulated time units of compliant operation to a standard for determining a compliant treatment factor for wound healing; and (i) leasing the pump at a payment schedule that is based at least in part on the compliant treatment factor.

18. The method as in claim 17, wherein the means for detecting compliant operation is a device for monitoring flow rate into the pump, comparing the flow rate to a reference flow rate, and indicating compliant operation when the flow rate is within a range of the reference flow rate.

19. The method as in claim 17, the pump being further adapted for reporting the recorded time units of operation and the recorded time units of compliant operation, the method further comprising the steps of:

requesting a report from the pump using the user interface, the report comprising an indication of one or more of said recorded time units of operation, said recorded time units of compliant operation, and said compliant treatment factor; and receiving the report from the pump using the user interface.

20. The method as in claim 19, further comprising the step of assessing a fee corresponding to the report.

21. The method as in claim 19, wherein the user interface comprises one or more of a keypad, a user-viewable display, and a data port for connecting to an electronic device.

22. The method of claim 17, where compliant operation is when suction is in a predetermined range about a pressure setpoint, wherein the pressure setpoint is a pressure value selectable by an operator.

23. The method of billing of claim 22, wherein the predetermined range about a pressure setpoint is a range of about ±25 mm Hg about the pressure setpoint.

24. A method of billing for usage of suction-assisted wound treatment system, comprising the steps of:

providing a system comprising a pump having a user interface for receiving input from a user on pump operation, a monitoring system, a reporting subsystem, and a timing subsystem;

measuring pump negative pressure from the wound using a flaw rate monitor;

detecting operation of the system using the flow rate monitor;

accumulating and recording time units of operation, by the timing subsystem;

determining, by the monitoring system, compliant time of operation of the system using the flow rate monitor, wherein compliant time of operation is time of operation of the pump when medically effective suction is being applied to a wound;

accumulating and recording time units of compliant operation, by the timing subsystem;

relating and reporting, by the reporting subsystem, the ratio of the recorded time units of compliant operation and the recorded time units of operation to a standard for determining a compliant treatment factor for wound healing; and billing at a payment schedule that is based at least in part on the compliant treatment factor and is based at least in part upon the recorded time units of operation.

25. A portable suction pump adapted for use in a suction-assisted wound treatment system, comprising:

a user interface to input data by a user, the data related to compliant operation of the pump, wherein compliant operation is operation of the pump when medically effective suction is being applied to a wound;

a monitoring system to monitor pump operation, said monitoring system including a flow rate monitor to determine compliant operation of the system, wherein the monitoring system is adapted to determine compliant operation of the pump; and a timing subsystem to record time units of compliant operation, a reporting subsystem for reporting the time units of compliant operation;

wherein the pump is leased on a payment schedule that is based at least in part on the recorded time units of compliant operation.

26. The pump as in claim 9, further comprising the user interface to request a report from the reporting subsystem and to receive the report from the reporting subsystem.

27. The pump as in claim 26, wherein a fee is charged corresponding to the report.

28. The pump as in claim 9, wherein the user interface comprises a keypad and a user-viewable display.

29. The pump as in claim 9, wherein the user interface comprises a data port for connecting to an electronic device adapted for requesting and/or receiving the report.

* * * * *